United States Patent
Rogers

(10) Patent No.: US 10,216,905 B2
(45) Date of Patent: Feb. 26, 2019

(54) HEALTH STATE TRENDS FOR A CONSISTENT PATIENT SITUATION

(71) Applicant: Google Inc., Mountain View, CA (US)

(72) Inventor: Jeffrey L. Rogers, San Carlos, CA (US)

(73) Assignee: Google LLC, Mountain View, CA (US)

( * ) Notice: Subject to any disclaimer, the term of this patent is extended or adjusted under 35 U.S.C. 154(b) by 309 days.

(21) Appl. No.: 15/008,295

(22) Filed: Jan. 27, 2016

(65) Prior Publication Data

US 2017/0351827 A1 Dec. 7, 2017

Related U.S. Application Data

(60) Provisional application No. 62/108,887, filed on Jan. 28, 2015.

(51) Int. Cl.
*G06F 19/00* (2018.01)
*A61B 5/0255* (2006.01)
(Continued)

(52) U.S. Cl.
CPC ........ *G06F 19/3418* (2013.01); *A61B 5/0255* (2013.01); *A61B 5/0507* (2013.01);
(Continued)

(58) Field of Classification Search
CPC ........ G06Q 50/22; G16H 10/00; G16H 10/20; G16H 10/40; G16H 10/60; G16H 10/65;
(Continued)

(56) References Cited

U.S. PATENT DOCUMENTS 4,838,275 A 6/1989 Lee
2002/0170193 A1* 11/2002 Townsend ............ A61B 5/1116
33/512
(Continued)

FOREIGN PATENT DOCUMENTS

JP 2001245856 9/2001
JP 2009517187 4/2009
(Continued)

OTHER PUBLICATIONS

"Preliminary Report on Patentability", PCT Application No. PCT/US2016/015267, dated Aug. 10, 2017, 7 pages.
(Continued)

*Primary Examiner* — Linh Giang Le
(74) *Attorney, Agent, or Firm* — Colby Nipper

(57) ABSTRACT

This document describes techniques and apparatuses enabling determination of health state trends for a consistent patient situation. Various noninvasive health monitors can be used to sense a patient's situation and health states, including disease progression, at those states. These noninvasive health monitors may also act passively and in a patient's normal course of life, which enhances many patient's desire to submit to monitoring, as well as increase consistency of use, as in many cases the patient does little or nothing to cause his or her health monitoring and health-trend determination. With health states determined for a consistent patient situation, more accurate and more robust health trends can be determined.

20 Claims, 8 Drawing Sheets

(51) Int. Cl.
    *A61B 5/05*     (2006.01)
    *A61B 5/08*     (2006.01)
    *A61B 5/11*     (2006.01)
    *A61B 5/00*     (2006.01)
    *G01S 13/88*     (2006.01)
    *G01S 7/41*     (2006.01)
    *G16H 50/30*     (2018.01)
    *A61B 5/01*     (2006.01)

(52) U.S. Cl.
    CPC ......... *A61B 5/0816* (2013.01); *A61B 5/1116* (2013.01); *A61B 5/1126* (2013.01); *A61B 5/4566* (2013.01); *A61B 5/4812* (2013.01); *A61B 5/7275* (2013.01); *G01S 7/415* (2013.01); *G01S 13/88* (2013.01); *G06F 19/00* (2013.01); *G16H 50/30* (2018.01); *A61B 5/0022* (2013.01); *A61B 5/01* (2013.01); *A61B 5/4842* (2013.01); *A61B 5/6891* (2013.01); *A61B 5/747* (2013.01); *A61B 2505/07* (2013.01); *A61B 2562/0247* (2013.01)

(58) Field of Classification Search
    CPC ........ G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00

See application file for complete search history.

(56) References Cited

U.S. PATENT DOCUMENTS

| | | | |
|---|---|---|---|
| 2005/0264303 A1 | 12/2005 | Bailey et al. | |
| 2008/0294019 A1* | 11/2008 | Tran .................. | A61B 5/0006 600/301 |
| 2009/0227882 A1* | 9/2009 | Foo .................. | A61B 5/0205 600/508 |
| 2010/0094174 A1* | 4/2010 | Choi .................. | A61B 5/1121 600/587 |
| 2010/0152600 A1* | 6/2010 | Droitcour ............. | A61B 5/05 600/534 |
| 2011/0087113 A1 | 4/2011 | Mack | |
| 2011/0112425 A1* | 5/2011 | Muhlsteff ............. | A61B 5/0507 600/534 |
| 2013/0002434 A1* | 1/2013 | Cuddihy .............. | G08B 21/043 340/573.7 |
| 2013/0053653 A1* | 2/2013 | Cuddihy .............. | A61B 5/0205 600/301 |
| 2013/0165770 A1* | 6/2013 | Li ...................... | A61N 5/1049 600/430 |
| 2013/0300573 A1 | 11/2013 | Brown et al. | |
| 2014/0194793 A1* | 7/2014 | Nakata ................ | A61B 5/0816 601/48 |
| 2014/0275834 A1 | 9/2014 | Bennett | |
| 2014/0340227 A1* | 11/2014 | Reed, Jr. ............. | A61B 5/6889 340/573.1 |
| 2014/0357961 A1 | 12/2014 | Meltzer et al. | |

FOREIGN PATENT DOCUMENTS

| | | | | |
|---|---|---|---|---|
| JP | 2011519288 | | 7/2011 | |
| JP | 2012120648 | | 6/2012 | |
| JP | 2014217453 | | 11/2014 | |
| KR | 10-2008-0083803 A | * | 9/2008 | ............. A61B 5/00 |
| KR | 20080083803 | | 9/2008 | |
| KR | 20110008080 | | 1/2011 | |
| KR | 10-2014-0006256 A | * | 1/2014 | ............. A61B 5/08 |
| WO | 2007143535 | | 12/2007 | |
| WO | WO 2007-143535 A3 | * | 12/2007 | ............. A61B 5/08 |
| WO | WO-2014113681 | | 7/2014 | |
| WO | 2016123287 | | 8/2016 | |

OTHER PUBLICATIONS

"Written Opinion", PCT Application PCT/US2016/015267, dated Aug. 4, 2016, 10 pages.

Lee, et al., "Monitoring and Analysis of Respiratory Patterns Using Microwave Doppler Radar", IEEE Journal of Translational Engineering in Health and Medicine; vol. 2, Nov. 18, 2014, 17 pages.

"Foreign Office Action", Korean Application No. 10-2017-7023571, dated Apr. 11, 2018, 9 pages.

"Foreign Office Action", dated Apr. 24, 2018, 4 pages.

"Foreign Office Action", Korean Application No. 10-2017-7023571, dated Oct. 26, 2018, 9 pages.

"Foreign Office Action", Japanese Application No. 2017539247, dated Nov. 6, 2018, 4 pages.

* cited by examiner

HEALTH STATE TRENDS FOR A CONSISTENT PATIENT SITUATION

PRIORITY APPLICATION

This application claims priority under 35 U.S.C. § 119(e) to U.S. Patent Application Ser. No. 62/108,887, titled "Health State Trends for a Consistent Patient Situation", and filed on Jan. 28, 2015, the disclosure of which is incorporated by reference herein in its entirety.

BACKGROUND

Medical evaluations are traditionally made through a trained provider doing a single or a few assessments. Typically these assessments are performed in a hospital or medical practitioner's office. These assessments are often incomplete, leading to missed disease detection in the early stages when treatment is more effective. This is due in part to assessments being made at some snapshot in a continuum of a patient's individual physiological rhythm, such as those of a patient's day (diurnal rhythms). These assessments may also fail due to being made during some particular situation during which the patient's health assessment can vary, such as due to stress caused by being at the practitioner's office.

These problems have been partially addressed through in-home monitoring. A patient can be given a monitoring device, such as a blood pressure cuff, which the patient can use to monitor his or her blood pressure at a particular time or at a consistent physiological state (e.g., in bed after waking up or right after breakfast). While this partial solution appears to address sporadic assessments, data shows that patients often do not remain diligent with home monitoring. Many patients will use a device for a while and then lose interest, only to suffer the negative health consequences. Other patients will use the device sporadically, missing some days, using the device at different times or in different states, and so forth. Still others will fail to use the devices correctly, giving inaccurate results. Even for those patients that use the monitoring device correctly, consistently, and over the long term, this partial solution still fails to monitor medical conditions early, as the monitoring devices are prescribed after a problem already exists. For these reasons, home monitoring when the user is actively required to perform the monitoring often fails to provide accurate medical assessments, especially over the longer term.

Further still, current medical assessments are negatively affected due to the variability intrinsic to the population and thus difficulties inherent in trying to calibrate health assessments to the individual.

SUMMARY

This document describes techniques and apparatuses enabling a more-complete evaluation of health state trends for a consistent patient situation, such as a person's cardiac vitals when the person is asleep. Various noninvasive health monitors can be used to sense a patient's situation, such as an activity, environment, emotion, or physiological state. These noninvasive health monitors may also act passively and in a patient's normal course of life, which enhances many patient's desire to submit to monitoring, as well as increase consistency of use, as in many cases the patient does little or nothing to cause his or her health monitoring and health-trend determination. With health states determined for a consistent set of patient situations, more-accurate and more-robust health trends can be determined. Thus, the technique may determine that a patient is asleep and at a particular point in his or her circadian rhythm and monitor the patient's heart daily and consistently at the same patient situation. By so doing, trends in the patient's heart health can be determined, even without that patient's active involvement or a need to calibrate the patient to population averages. These trends can save the patient's life by forecasting negative health trends that lead to congestive heart failure.

This summary is provided to introduce simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices enabling determination of health state trends for a consistent patient situation are described with reference to the following drawings. The same numbers are used throughout the drawings to reference like features and components.

DETAILED DESCRIPTION

Overview

Figure 1:
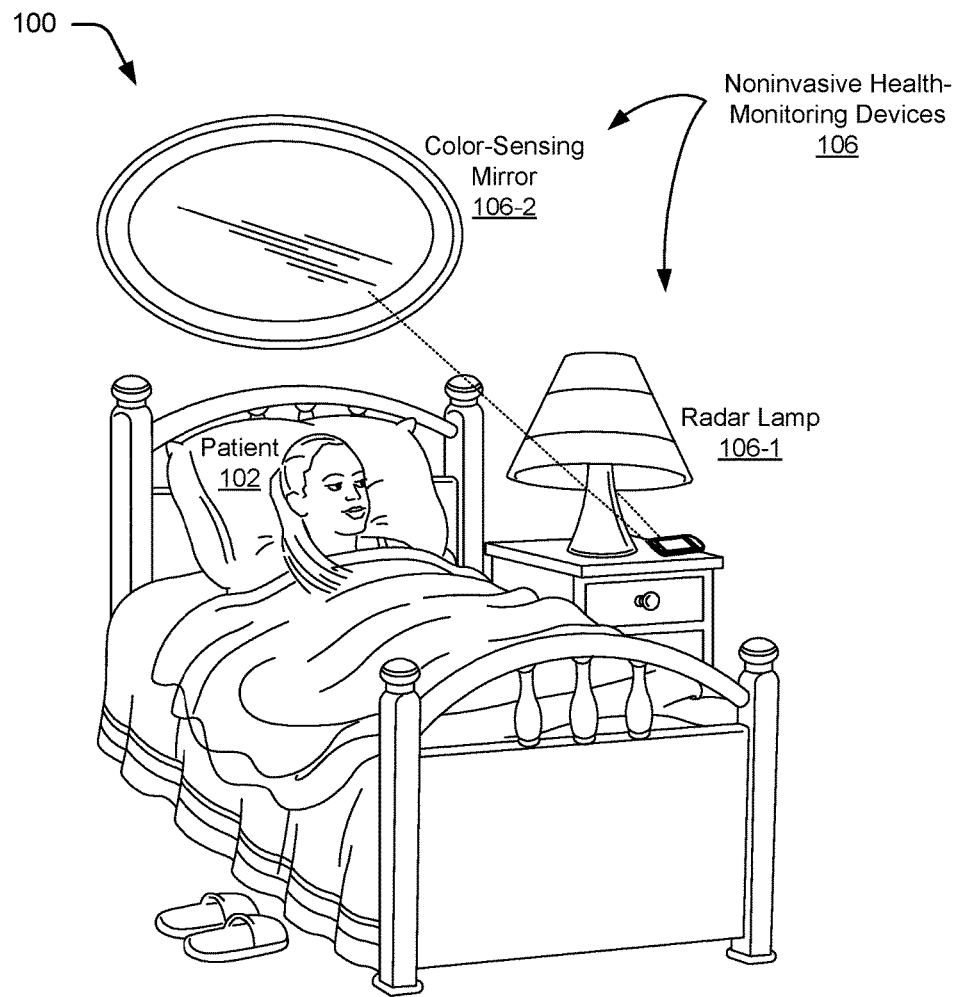
FIG. 1 illustrates an example environment in which the techniques can be implemented.

This document describes techniques and devices enabling determination of health states and trends in these states that allow the detection of disease progression. By assessing health states of the patient frequently relative to the evolution timescale of disease, health trends can be identified and used to manage patient wellness. Not only is this information valuable to a patient's medical professional due to its accuracy and robustness, it is also valuable because it provides patients with real data about them. This data about them, rather than averages, demographics, or generalized prognosis from medical professionals, is more likely to prompt the patient to act to maintain or improve their own health. Evaluating the user or patient when they are in a similar condition, e.g., in deep sleep or during exercise, facilitates comparison between individual measurements and reduces the need for calibrating the health measurements and models to the individual.

By contrast, consider the accuracy and robustness of a health trend determined through monitoring at a medical office or hospital. Assume that four different tests are performed at the hospital or medical office over a two-month period; a patient's blood pressure is measured once in the morning, once in the afternoon, once after the patient has had too much caffeine, and once after a night of poor sleep. Each of these different tests was performed during different situations for the patient. A trend based on these four tests is therefore suspect due to these varying patient situations.

Consider also medical advice based on averages and demographics. Many patients ignore medical advice based on averages and demographics because it isn't really about them. When given good advice based on demographics and averages, for example, many people do not follow this advice or don't follow it for long enough because they do not see the benefit. When people take the advice of changing their diet and habits—which most people do not want to do—they often don't see the improvement. They may see that they have lost weight and so forth, but these are not precise measures of their health. Because of this, many people go back to their old habits only to suffer from that failure.

By way of one example of the techniques described herein, assume that a patient has three noninvasive health-monitoring devices in her bathroom. These three are a mat in front of her bathroom sink, a toilet-seat sensor, and a mirror over her bathroom sink. Each of these devices can be used to measure the patient's situation and health state, alone or together. Thus, the mat can measure her body's electrical behavior to provide an electrocardiogram, the toilet-seat sensor can measure pressure pulses as blood flows through the body to characterize the mechanical motion of the heart and blood flow, and the mirror over her sink, using a radar-based sensor or a color camera, can measure capillary blood flow or skin color variations, which can indicate differential blood volume to provide a photo-plethysmogram.

Each of these physiological signals can provide insight into a state of health, however these states are dependent on the diurnal rhythms, activity level, and environmental conditions at the moment of health assessment. For example, health assessments can be made daily during similar situations, such as when the patient has just gotten up from bed, at a same time of day, or when sitting down to breakfast. The patient situation may also be based on a physiological state, such as when the patient has a heart rate of between 100 to 104 beats per minute, is standing rather than sitting or lying down, and so forth. Note that this patient does not have to do something outside of her normal course of life—simply washing her face while standing on the mat, looking into the mirror, and using the toilet provide opportunities for these three devices to sense her vitals and physiological signals. Pulling together these quantities to provide the most useful data into models of her health provides an assessment that can be compared to prior health data. Thus, identifying health trends is more manageable by assessing the patient when they are in a similar patient situation, activity level, and in similar environmental conditions to the previous assessments.

The techniques may then determine a health state trend for a consistent patient situation and provide this to the patient or practitioner. Assume that over the course of a new diet and exercise routine that the techniques determine a health state trend where a patient's heart health as measured by heart-stroke volume (an important measure of cardiac health) has improved 6% in four weeks. With this positive feedback, this patient may continue her diet and exercise routine, thereby likely reducing the chances that she will die prematurely of heart disease. Conversely, if a trend of rising blood pressure is noted she can be provided suggestions on limiting her salt intake to lower her blood pressure.

These are but examples of ways in which determination of health state trends for a consistent patient situation can be performed. Other examples, such as radar-based sensing of deep sleep, are provided below. This document now turns to an example environment, after which example noninvasive health-monitoring devices and methods, and an example computing system are described.

Example Environment

FIG. 1 is an illustration of an example environment 100 in which health state trends for a consistent patient situation can be employed. Environment 100 illustrates a patient 102 that is the subject of the health monitoring, as well as a medical professional 104 that, in some cases, will receive results of the health monitoring. This example employs noninvasive health-monitoring devices 106 (devices 106), including a radar-based health-monitoring lamp 106-1 (radar lamp 106-1) and a color-sensing mirror 106-2. Other example noninvasive health-monitoring devices 106 are illustrated in later figures.

Sensor data 108 is provided by each of devices 106 to some computing device, such as a computing device 110, which then performs some or all of the techniques, or passes that sensor data to some other computing device, such as a remote server through a communication network (not shown).

As shown with this example environment 100, a sensing milieu (e.g., devices 106 in patient 102's bedroom) in which a patient lives can be used that, through one or multiple devices, is capable of determining a patient's situation, such as the patient's activity or activity level, environment, emotion, or physiological state. This sensing milieu is capable of determining this patient situation and health states without actually measuring the patient through an invasive test. This sensing milieu senses various states and conditions of the patient, which can then be correlated, aggregated, and so forth to determine health states at a consistent patient situation, and thus trends in a patient's health for that state. The techniques are described in the context of cardiovascular and skeletal systems, though health trends for other physiological systems can be measured, such as endocrine, muscular, nervous, and integumentary systems. These techniques can, for example, detect an impending heart failure by identifying cardiovascular decompensation before it is evident to the patient or healthcare provider looking for clear symptoms, such as increasing body weight.

In addition to the sensing milieu noted above (a bedroom), consider also a person's automobile. An automobile seat can include various sensors, such as fiber optics or piezoelectric materials configured to sense heart beats and respiration. The automobile's rear-view mirror can include a camera operating similarly to color-sensing mirror 106-2. The automobile may also include a radar sensor similar to radar lamp 106-1 to locate persons, sense heart and respiration rates, and so forth. Thus, sensing milieus are not limited to stationary scenarios or some particular example, whether a person's bedroom, bathroom, office, workplace, or automobile.

In more detail, a patient's health state is a functional state of a patient's health that is capable of being determined for a patient over multiple iterations and over a non-immediate temporal period. A health state describes the health of an individual or of component systems within a person. For example, the state of a person's cardiovascular system is ultimately determined by its ability to achieve proper organ perfusion and molecular gas exchange. These functional metrics can be parameterized by cardiac pressures and volumes (i.e., measures of cardiac performance) and the rate at which blood flows through the vascular (i.e., pulse wave velocity). Vitals including hearts rates and respiration rates, along with patient situations to aid in assessing health state trends. Example diurnal patient situations include rapid eye movement (REM) sleep, non-REM sleep (including three stages, slow-eye-movement (SEM) sleep, no-eye movement sleep, and deep sleep, also called slow-wave sleep (SWS), which begins when delta waves occur), skeletal orientation, body movements, and so on. Patient situations may also include activity levels associated with acts like getting out of bed, urinating, bowel movements, showering, eating, walking, and other repeated situations for the patient, such as coming home from work, reading a book, watching television, playing a video game, exercising, and so forth.

Figure 2:
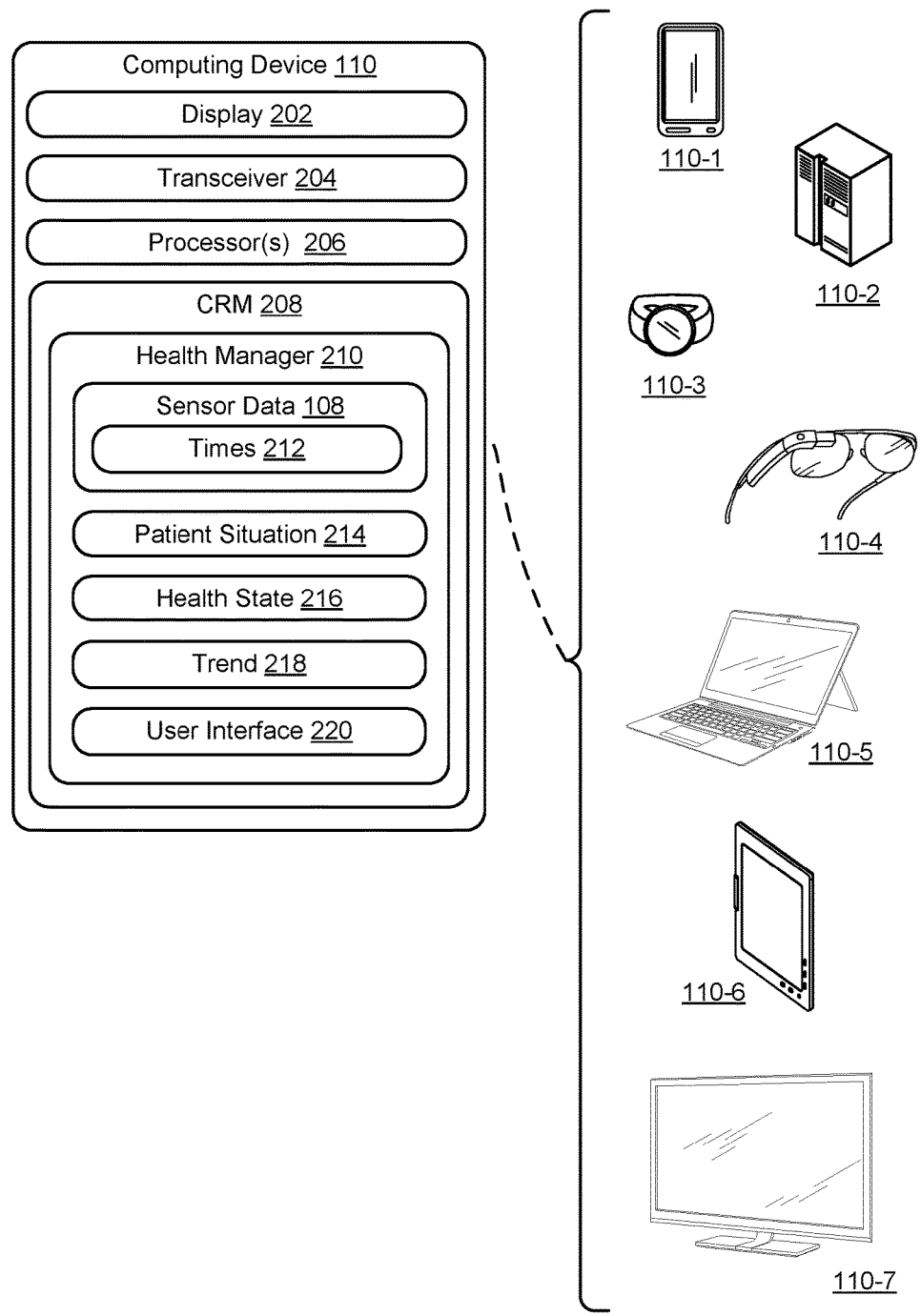
FIG. 2 illustrates an example computing device of FIG. 1.

With regard to the example computing device 110 of FIG. 1, consider a detailed illustration in FIG. 2. Computing device 110 can be one or a combination of various devices, here illustrated with seven examples: a smartphone 110-1, a server 110-2, a computing watch 110-3, computing spectacles 110-4, a laptop 110-5, a tablet computer 110-6, and a computing television 110-7, though other computing devices and systems, such as a netbook or desktop may also be used. As noted above, in some embodiments the techniques operate, in whole or in part, through a remote device such as server 110-2. In such cases, some computing can be forgone locally, e.g., through a communication device having limited computing operations or even directly from devices 106 to server 110-2.

Computing device 110 includes or is able to communicate with a display 202 (six are shown in FIG. 2), a transceiver 204, one or more processors 206, and computer-readable storage media 208 (CRM 208). Transceiver 204 is capable of sending and receiving data directly or through a communication network, such as sensor data 108 from devices 106 through a local area, wide area, personal area, cellular, or near-field network.

CRM 208 includes health manager 210, which includes or has access to sensor data 108, which may include sensor data 108 from one or multiple devices 106. This sensor data 108 can be associated with particular times 212 (e.g., respective time data), such that temporal proximity to patient situations 214 can be determined. Generally, patient situations 214 include an activity, emotion, environment, or physiological state. Activities include, for example, sleeping, walking, eating, working, exercising, driving, and talking. Emotions include any emotion that can be sensed by a device, such as sensors of computing device 110 or noninvasive health-monitoring devices 106, e.g., fear, nervousness, calmness, and apathy. Environments are those in which a patient may be in, whether of a particular type or an identical location, such as at work generally or specifically at patient 106's desk, in a car, in a subway car, train, or bus, out to dinner or a movie, in a park, or at home. Physiological states include deep or REM sleep, particular heartrates, and so forth (various examples of these are provided herein).

Sensor data 108 can be used to determine vitals and patient situations 214 or health states 216 or both. Health states 216 for a particular patient situation 214 can be used to determine a health state trend 218 for that state. This health state trend 218 can be determined based on an amount of time or a number of consistent patient situations at which health states were determined. CRM 108 also includes or has access to a user interface 220, which, while not required, can be used to present determined trends, health, and medical advice to patient 102.

Generally, health manager 210 is capable of determining, based on sensor data 108, a set of patient conditions and a health state of a patient, such as patient 102 of FIG. 1. With multiple health states for a consistent patient situation, health manager 210 determines a health state trend for the patient. Assume, for example, that a health state measured six months ago indicates a particular pressure-volume loop for the patient's heart performance during exercise. But currently, now six months later, the pressure-volume loop for the patient during a similar exercise indicates a different pressure-volume loop. The difference between the loops, along with trends in vitals (e.g., heart rate) and thoracic fluid can indicate many different health trends, such as a congestive heart failure likely to occur within the next 60 days. Note the current pressure-volume loop or any of the individual vitals or physiological parameters may not on its own indicate any likely heart failure to a medical professional. Instead, the difference over time for a same patient situation indicates this likely heart failure even when the current pressure-volume loop may be within a normal range for the population.

Figure 3:
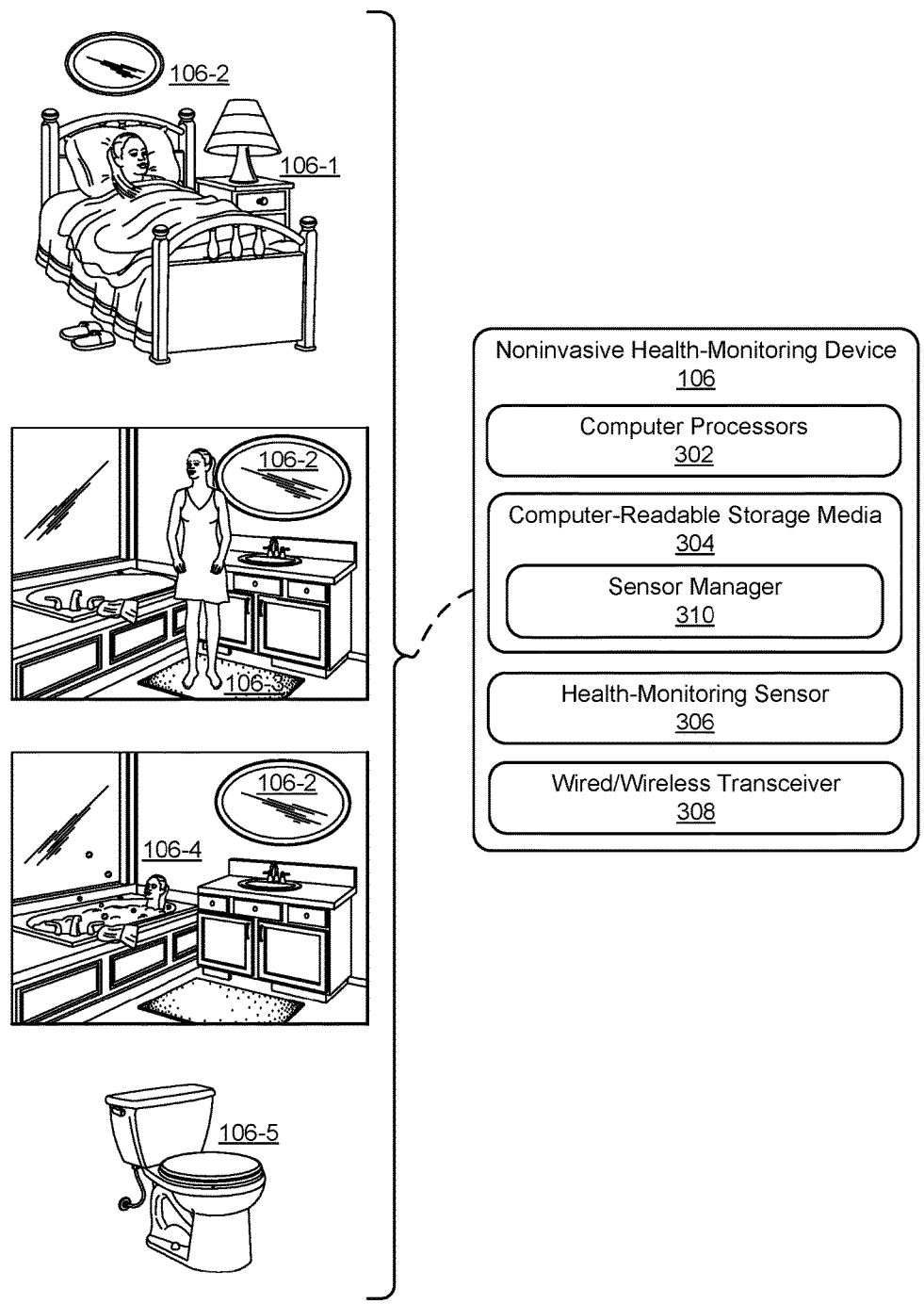
FIG. 3 illustrates example noninvasive health-monitoring devices of FIG. 1.

With regard to noninvasive health-monitoring devices 106, two examples of which are shown in FIG. 1, consider a detailed illustration in FIG. 3. Noninvasive health-monitoring device 106 can be one or a combination of various devices, here illustrated with five examples: radar lamp 106-1, color-sensing mirror 106-2, pressure and electrical-sensing mat 106-3 (mat 106-3), ultrasonic bathtub 106-4, and pressure-sensing toilet seat 106-5 (toilet 106-5).

These noninvasive health-monitoring devices 106 can also be passive in the sense that a patient's explicit interaction is not needed—the patient need not pick up the sensor, intentionally stand on a weight scale, or select some sensor to do something. While passive in this sense, some of these devices sense a patient's health state through sending out sound waves (e.g., ultrasonic bathtub 106-5), electromagnetic waves, electrical signals, uniform illumination (e.g., mirror 106-2), and millimeter and similar radiation (e.g., radar lamp 106-1). Others of these devices can forgo even use of waves, signals, and radiation, such as sensing pressure of patient 102's blood through toilet 106-5.

Noninvasive health-monitoring devices 106 may have various computing capabilities, though they may instead be a low-capability devices having little or no computing capability. Here device 106 includes one or more computer processors 302, computer-readable storage media 304, a health-monitoring sensor 306, and a wired or wireless transceiver 308 capable of receiving and transmitting information (e.g., to computing device 110). Each of noninvasive health-monitoring devices 106 may include a different health-monitoring sensor 306 having same or different modalities in which to measure a patient's health state or patient situation and other aspects. Computer-readable storage media 304 includes sensor manager 310, which is capable of processing sensor data and recording and transmitting sensor data for a health-monitoring act.

Figure 4:
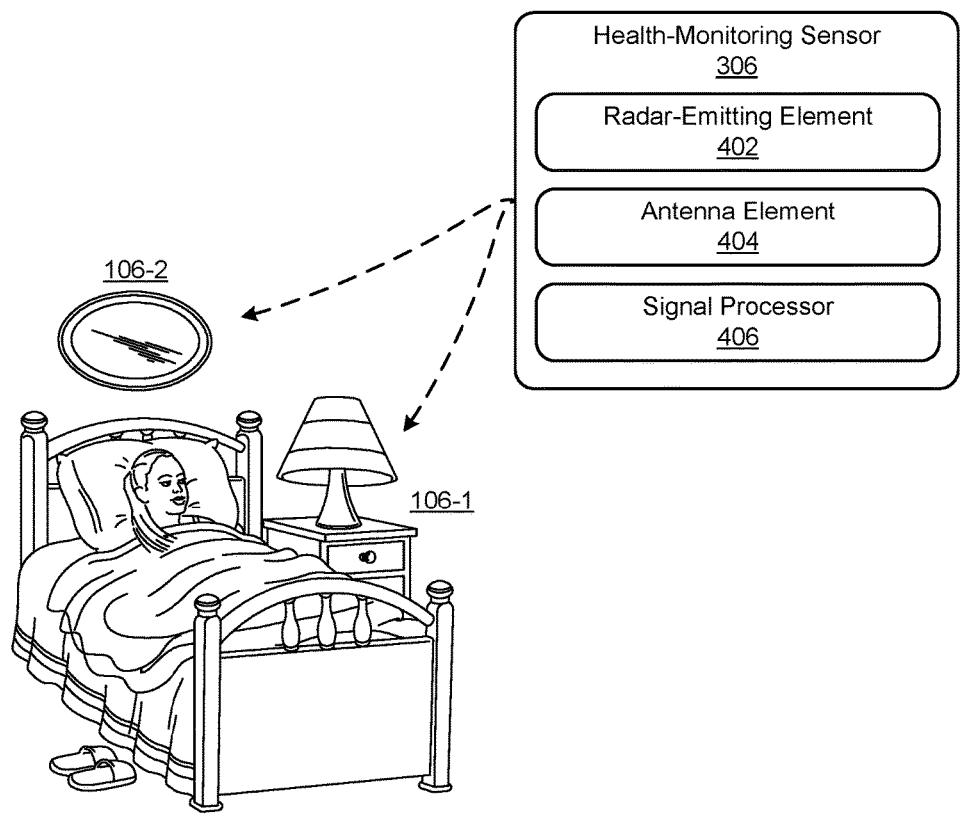
FIG. 4 illustrates a radar-based example of the health-monitoring sensor of FIG. 3, including within the radar lamp and mirror of FIG. 1.

Consider, for example, FIG. 4, which illustrates a radar-based example of health-monitoring sensor 306 that can be included within radar lamp 106-1 or color-sending mirror 106-2. Health-monitoring sensor 306, as noted above, is configured to sense health states and patient situations, through use of a radar field in this particular case. To enable sensing, health-monitoring sensor 306 includes a radar-emitting element 402, an antenna element 404, and a signal processor 406.

Radar lamp 106-1 and/or color-sensing mirror 106-2 are configured to reflect radiation from human tissue to measure skin temperature and perspiration, heart rate, and skeletal movement, to name just four examples. Radar lamp 106-1 includes radar-emitting element 402, which provides a radar field configured to reflect from human tissue and penetrate non-human material, such as through continuously modulated radiation, ultra-wideband radiation, or sub-millimeter-frequency radiation. These reflections can be received by an antenna element 404 and then processed by a signal processor 406 to provide sensor data 108. This radar field can reflect from human tissue, such as skin, bone, or heart muscle. Assume, for example, that patient 102 is asleep and radar lamp 106-1 is integral with a lamp on her nightstand. Normally people move around throughout their day and thus sensor data can be unreliable or noisy. In the case of sleep, however, radar lamp 106-1 measures patient 102's chest deflections to record respiration rate. These chest deflections include wiggles or perturbations caused by patient 102's heartbeat and thus a heart rate can also be calculated.

In more detail, a radar field provided by radar-emitting element 402 can be a small size, such as about one millimeter to about 1.5 meters, or an intermediate size, such as about one to about 30 meters. In the intermediate size, antenna element 404 or signal processor 406 are configured to receive and process reflections of the radar field to provide large-body states or conditions based on reflections from human tissue caused by body, arm, or leg movements. Antenna element 404 can include one or many antennas or sensors, such as an array of radiation sensors, the number in the array based on a desired resolution and whether the field is a surface or volume. The antenna element can also include either mechanical or electronic beam steering. For example, a phase gradient across the array of emitters could be used to direct the beam to a region of interest as the person sleeping moved, thereby allowing both continuous sensing and distinguishing between multiple people in one bed. Signal processor 406 is configured to process the received reflections within the radar field to provide sensor data usable to determine a set of patient conditions or health state.

By way of example, some patient situations and other aspects of a patients' conditions provide substantial value in what health states can be shown. Consider deep sleep. At deep sleep a patient's cardiac and nervous systems are in a unique position. A heart rate variability (e.g., cardiac rhythm or variance in the cardiac rhythm) and respiration rate, when measured during deep sleep, provide a unique window into the patient's cardiac health, especially when trends are shown for multiple sessions of deep sleep.

Returning to FIG. 3, consider each of the other example devices 106 in more detail. Pressure and electrical-sensing mat 106-3 is configured to sense a pulse transit time or pulse-wave velocity of patient 102's blood. This pulse-wave velocity can be used in determining characteristics of a pressure-volume loop for the patient's heart. This pulse-wave velocity is also a measure of a patient's vascular health. In healthy arteries of the cardiovascular system the pulse-wave velocity is low due to the elasticity of the arteries but, as they harden and narrow, the pulse-wave velocity rises. While a particular pulse-wave velocity is a snap shot in time that may or may not accurately indicate vascular health (e.g., a one-time test at a doctor's office), a change in this pulse-wave velocity (that is, a trend), can be an accurate measure of a change in patient 102's cardiovascular health. Trends can be determined without the need for calibration to the individual patient (e.g., removing the need for measuring an individual's aortic diameter to understand their heart function). If a positive trend, this can reinforce patient 102's healthy habits and, if negative, encourage changes to be made.

Mat 106-3 may also measure a heart's electrical conduction system through electrical impulses generated by the polarization and depolarization of cardiac tissue, and then translate this to a waveform (alone or by another entity). Measurements alone, or trends over time, can indicate hypercalcemia, hypocalcemia, hyperkalemia, hypokalemia, coronary ischemia, or myocardial infarction (i.e., a heart attack). Note also that trends found through data sensed by devices 106 can determine a negative heart or other system condition sooner than may not otherwise be found, thereby catching a decline in health early enough to counter it and avoid more invasive and risky treatment. For example, increases in an individual's resting heart rate, along with increases in thoracic fluid, changes in cardiac rhythm variability, or other physiological characteristics can alert of an impending heart failure decompensation two weeks or more in advance of that failure. This alert permits a medical professional, or the patient herself, to avoid the decompensation, such as through new or altered medications.

Ultrasonic bathtub 106-4 is configured to generate high-frequency sound waves and to evaluate an echo from those waves. This echo is received at one or more sensors and the time interval between sending and receiving can be measured. These echoes enable analysis of internal body structures. In some cases, acoustic impedance of a two-dimensional cross-section of tissue can be measured, which can measure current heath or a health trend of the measured tissue. Blood flow, tissue movement, blood location, and three-dimensional measurements of structures can also be made. Non-active (no sound waves generated, just receiving sensors) can also be used, though accuracy and robust measurements are more difficult to achieve.

Pressure-sensing toilet seat 106-5 is configured to sense pulse-wave velocity as noted for mat 106-3 above, but can also study the heart on different conditions, such as measuring cardiovascular health through bowel movements, which are similar to a Valsalva maneuver (named after surgeon Antonio Maria Valsalva, 1666-1723) used by some cardiologists to measure heart reactivity.

Color-sensing mirror 106-2 can be configured to sense colors in a patient's skin, either with or without a radar field of FIG. 4, such as with a color-sensing camera. This sensor data can be sufficient to determine a photo-plethysmogram, which is one of the key physiological signals to determine of a patient's health. A plethysmogram measures variations in a size or color of an organ, limb, or other human part from changes in an amount of blood present in or passing through it. These colors and color variations in a patient's skin can show heart rate and efficiency. Further, color-sensing mirror 106-2 may also radiate (through radar or other radiation bands), at low and safe levels, patient 102 and sense the backscatter from the radiation, thereby determining more robustly or accurately patient 102's integumentary, muscular, or cardiovascular system health and efficiency.

These examples show some ways in which the techniques can provide sensor data by which to determine patient situations and health states in a patient's normal course of life. As noted, conventional health monitoring is often performed at a hospital or medical practitioner's office. Health monitoring at a hospital or office, however, cannot monitor a patient during their normal course of life as they move through diurnal rhythms and stresses from activity, emotions, and environmental conditions. This can be a serious limitation because a snapshot captured at a hospital or office may not accurately reflect the patient's health. This can be due to the testing being of a short duration or due to the testing being in an artificial environment.

These and other capabilities, as well as ways in which entities of FIGS. 1-4 act and interact, are set forth in greater detail below. These entities may be further divided, combined, and so on. The environment 100 of FIG. 1 and the detailed illustrations of FIGS. 2-4 illustrate some of many possible environments capable of employing the described techniques.

Example Methods

Figure 5:
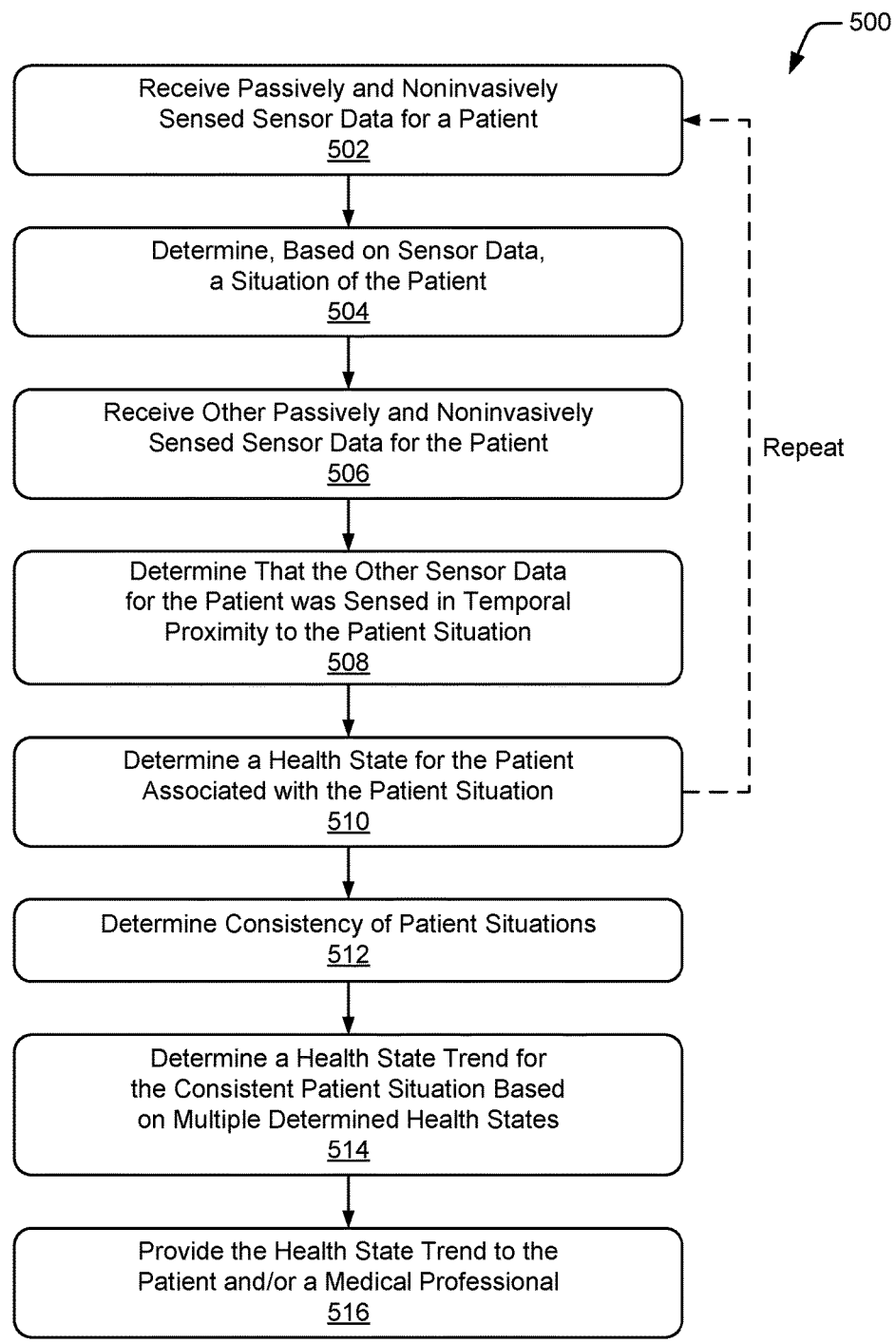
FIG. 5 illustrates a method for determining a health state trend for a consistent patient situation.
Figure 6:
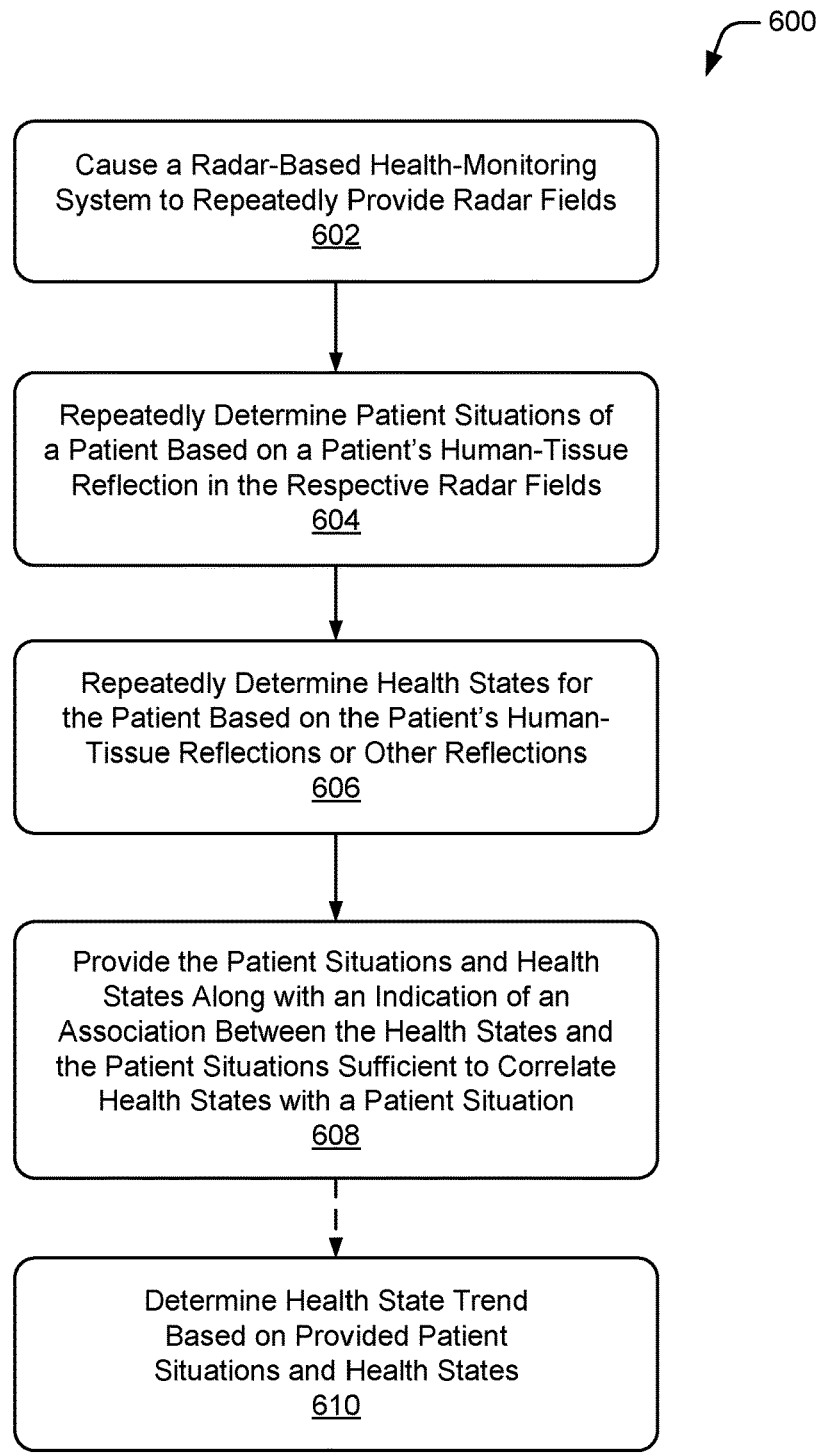
FIG. 6 illustrates a method in which a radar-based health-monitoring system is used to determine health state trends for a consistent patient situation.

FIGS. 5 and 6 depict methods 500 and 600 that enable determination of health states and health trends for a consistent patient situation. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2-4, reference to which is made for example only. The techniques are not limited to performance by one entity or multiple entities operating on one device.

At 502, passively and noninvasively sensed sensor data is received for a patient. This sensor data can be sensed in a patient's normal course of life, also referred to as in-vivo, meaning "in life." This is in contrast to in an artificial environment, such as medical offices and hospitals, which can induce anxiety, lack sufficient numbers of tests due to practicality concerns, or be subject to sensing during multiple or unknown patient situations of a patient. As noted in part above, this and other sensor data (at various operations in methods 500 and 600) can be passively and noninvasively sensed. Noninvasive sensor data is sensed without piercing a patient's skin or orifice and passively sensed sensor data is sensed without active and explicit participation from the patient.

At 504, a patient situation and other aspects of the patient conditions are determined based on the passively and noninvasively sensed sensor data received for the patient. As noted above, a patient situation of a patient is a condition or situation relevant to a patient's health that is capable of being determined for a patient over multiple iterations and over a non-immediate temporal period. Various example states are described above as part of FIGS. 1-4.

At 506, other passively and noninvasively sensed sensor data is received for the patient. This sensor data, and other sensor data for methods 500 and 600, can be received through a transceiver and from noninvasive health-monitoring devices 106.

At 508, the other passively and noninvasively sensed sensor data received at operation 506 is determined to be sensed in temporal proximity to the sensor data used to assess the patient situation. This is trivial if the sensor data for operations 502 and 506 are the same. If different sensor data, this temporal proximity can be immediate or a same time, or can vary based on the physiological condition. Thus, for a deep sleep lasting minutes or longer, the temporal proximity may last for minutes after a time at which sensor data used to determine that the patient situation was sensed. For a shorter assessment, the temporal proximity can be narrow, such as a patient situation in the process of standing up from a seated position being at or immediately after (e.g., in the case of a heart rate measured right at or after a patient stands up being associated with the state of standing up from a seated position). Note that in some cases the sensor data may be determined to not be sensed in temporal proximity, or otherwise determined to not be accurate, valuable, or useful. In such a case the techniques may forgo use and storage of such data.

At 510, a health state for the patient associated with the patient situation is determined using passively and noninvasively sensed sensor data received for the patient and sensed in temporal proximity to the patient situation. Note that this sensor data can be the same or different from sensor data received at operation 502. Further, this sensor data can be from a same or different health-monitoring device 106, such as sensor data 108 from color-sensing mirror 106-2 and sensor data 108 from radar lamp 106-1 where one is used to determine patient situation 214 and another health state 216. For sensor data 108 that is different for operations 502 and 506, the sensor data 108 may be of different modalities, such as reflected light, sound waves, electromagnetic sensing, radar, or fluid mechanics. As noted in part herein, these health assessments can vary from heart rate, respiration rate, blood oxygen content, bone density, and many others, and can measure a health of a physiological system, though specific adherence to a particular system is not required. By way of example, the techniques may determine that patient 102 is in a deep sleep (stage 3 delta-wave or SWS sleep) by cardiac rhythm and respiration rate, eye movement, and/or delta wave detection, the health state is an oxygen content of the patient's blood, and the health state trend is a change over time and iterations of the health state of the oxygen content of the patient's blood.

Following operation 510, method 500 may repeat one or more times to determine additional health states for a consistent patient situation and other patient conditions, such as deep sleep or a heart rate having a range from 118 to 122 beats per minute and so forth. This repeating is shown with a repeat arrow in FIG. 5. How many times it is repeated can depend on various factors, such as a period of time (e.g., weeks or months) or a number of health states determined for a consistent patient situation (e.g., 10 or 100).

At 512, a consistency of patient situations is determined. This consistency can be determined based on the states being equivalent or substantially equivalent, such as a heart rate state of 120 being equivalent at 120 and substantially equivalent at 118 to 122. This consistency can also be based on the medical parameters for the patient situation, and thus can vary. A patient situation, as noted above, can be broad or narrow, and thus the trend determined based on it can be more or less accurately tied to a particular physiological, activity, emotion, and environment factors for a patient. This state can also be more or less narrowly defined and thus the consistency based on how long a medical professional considers wise to monitor the patient. A patient suffering from an acute disease state or in a poor health generally, may indicate that a broader parameter of consistency is permitted, as it will likely take less time to gain statistically relevant samples for the health state. Some patient situation parameters can be tailored or selected well after the sensing is complete to tailor the health state trend to a broad or narrow consistency of the patient of patient conditions. For example, a state of a patient having a bowel movement, as sensed by toilet 106-5, can be considered a same state as another bowel movement regardless of when, or greater consistency can be used, such as only those that are within one hour of the patient getting out of bed.

At 514, a health state trend for the patient situation of the patient is determined based on the health state for the patient at multiple iterations of the first and second determining steps and for the consistent patient situation, such as various prior-determined and a current health state for that set of conditions. This can be as simple as a trend line from vitals (e.g., a certain heart rate), bone density, or spinal curve to more complex trends, such as a change to a shape of a pressure-volume loop for a patient's heart. It may also involve identifying a specific disease state, tracking disease progression, and calculating likely outcomes based on specific actions by the patient.

At 516, the health state trend for the patient's situation is provided effective to enable determination of the patient's health at the consistent patient situation. In some cases, this trend is provided to medical professional 104 or to patient 102 through presentation in user interface 220 of computing device 110 by health manager 210 (all of FIG. 1 or 2). Alternately or additionally, patient 102 may provide input via user interface 220 effective to cause transmission of the health state trend or health data to medical professional 104.

Using the example of FIGS. 1-4, noninvasive health-monitoring devices 106 of FIG. 3 sense, through health-monitoring sensor 306, various sensor data 108. This sensor data 108 is then transmitted to computing device 110 through wired/wireless transceiver 308. The transmitted sensor data 108 is received from one or more of devices 106 of FIG. 3 at transceiver 204 of computing device 110. Health manager 210 then determines patient situations and other patient conditions, health states, trends for health states having a consistent patient situation of patient conditions, and provides that trend, such as through user interface 220 of computing device 110.

FIG. 6 depicts method 600, which describes manners in which a radar-based health-monitoring system is usable to determine health state trends for a consistent patient situation, such as changes in cardiac vitals during deep sleep over months or years.

At 602, a radar-based health-monitoring system is caused to repeatedly provide radar fields. These can be any of those described herein. By way of one example, consider a skeletal system of an elderly woman. This physiological system is responsible for substantial numbers of deaths and decreased health in the elderly. Radar lamp 106-2 of FIGS. 1, 3, and 4, for example, can be used to sense patient 102's health state (here a spine curvature) and patient situation of patient conditions (here lying in bed). These radar fields can reflect from human tissue as noted above, thereby sensing a patient's situation or health.

At 604, patient situations are repeatedly determined based on a patient's human-tissue reflection in the respective radar fields. As described in FIG. 4 and method 500, radar-emitting element 402 provides radar fields, antenna element 404 receives reflections, and signal processor 406 processes these reflections to provide sensor data 108. Sensor data 108 can be analyzed to determine that patient 102 of FIG. 4 is lying down, for example.

At 606, health states for the patient are repeatedly determined based on the patient's human-tissue reflection or another human-tissue reflection in the respective radar fields. Similarly to operation 604, sensor data 108 can be analyzed to determine that patient 102 has a particular spinal curvature. As a snapshot, this may or not be meaningful, as it would depend on the way patient 102 lies, the softness of her bed, and forth. For a consistent state—the same bed and lying on her back (rather than side, etc.), changes in the curvature of her spine can indicate a trend of positive or negative back health, such as osteoporosis. Various sleep states and health states can also be determined, as noted above, with radar-based (or other types of) health-monitoring devices 106.

At 608, the patient situations and the health states, along with an indication of an association between each of the health states and the patient situations, are provided sufficient to correlate multiple health states with at least one of the patient situations and other aspects of the set of patient conditions. As noted, these can be provided to patient 102 through a device's user interface, such as computing device 110, or to medical professional 104.

Optionally, at 610 the health state trend is determined based on the provided patient situation, other patient conditions, and health state. Consider again health-monitoring devices 106 of FIG. 3 and the example health-monitoring sensor 306 of FIG. 4. In some cases noninvasive health-monitoring device 106, through sensor manager 310, is capable of determine health state trends, either alone or in combination with other entities (such as health manager 210 of FIG. 2). In such a case, the health state trend is provided to some entity for later use.

Figure 7:
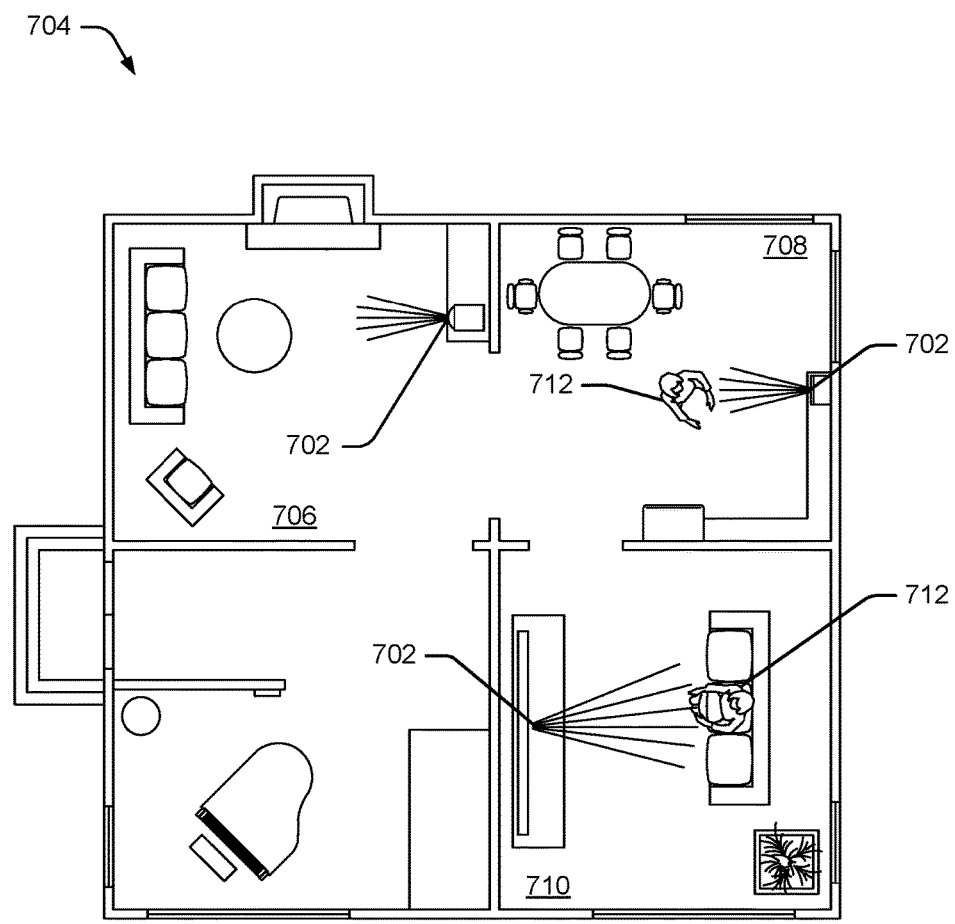
FIG. 7 illustrates a main floor of a house in which radar-based noninvasive health-monitoring devices are placed.

By way of another example, consider FIG. 7, which illustrates three additional radar-based health monitoring devices 702 on a main floor of a house 704. As shown in FIG. 7, health monitoring devices 702 are placed in living room 706, kitchen 708, and media room 710. These devices can sense woman 712's height, skeletal shape, and body movement and various situations and states she may be in. With these measurements from various radar-based devices, health manager 210 (with sensor data 108 from one or more of devices 702) determines various patient situations and health states, and thus trends of woman 712's skeletal system. These trends can indicate osteoporosis or a failing knee or hip joint and thus medicine or lifestyle changes that the woman can undergo to slow this negative trend or avoid risk factors for these problems.

While the above method 600 is described in the context of a skeletal system, the techniques are not limited to skeletal systems, as other systems and health state trends not fitting a particular system can be determined. A cardiovascular health trend determined through a consistent deep-sleep patient situation, for example, can be determined through the techniques, thereby providing valuable information about a patient's health that is difficult if not impossible to ascertain through artificial health monitoring at a medical office or hospital.

The preceding discussion describes methods relating to determination of health state trends for a consistent patient situation. Aspects of these methods may be implemented in hardware (e.g., fixed logic circuitry), firmware, software, manual processing, or any combination thereof. These techniques may be embodied on one or more of the entities shown in FIGS. 1-4, 7, and 8 (computing system 800 is described in FIG. 8 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 8:
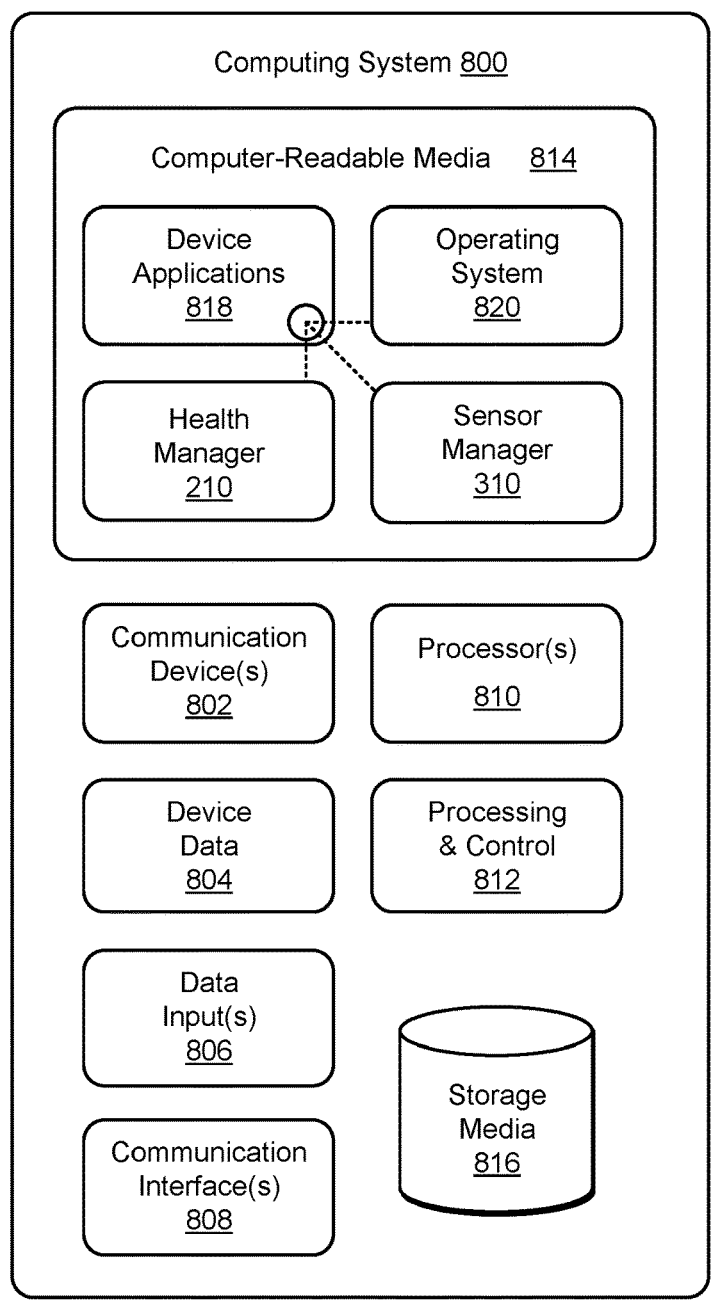
FIG. 8 illustrates an example device enabling determination of, or in which techniques may be implemented that determine, health state trends for a consistent patient situation.

FIG. 8 illustrates various components of example computing system 800 that can be implemented as any type of client, server, and/or computing device as described with reference to the previous FIGS. 1-7 to determine health state trends or disease progression for a consistent patient situation of patient conditions. In embodiments, computing system 800 can be implemented as one or a combination of a wired and/or wireless wearable device, System-on-Chip (SoC), and/or as another type of device or portion thereof. Computing system 800 may also be associated with a user (e.g., a patient) and/or an entity that operates the device such that a device describes logical devices that include users, software, firmware, and/or a combination of devices.

Computing system 800 includes communication devices 802 that enable wired and/or wireless communication of device data 804 (e.g., received data, data that is being received, data scheduled for broadcast, data packets of the data, etc.). Device data 804 or other device content can include configuration settings of the device, media content stored on the device, and/or information associated with a user of the device. Media content stored on computing system 800 can include any type of audio, video, and/or image data, including complex or detailed results of human-health-monitoring acts. Computing system 800 includes one or more data inputs 806 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 800 also includes communication interfaces 808, which can be implemented as any one or more of a serial and/or parallel interface, a wireless interface, any type of network interface, a modem, and as any other type of communication interface. Communication interfaces 808 provide a connection and/or communication links between computing system 800 and a communication network by which other electronic, computing, and communication devices communicate data with computing system 800.

Computing system 800 includes one or more processors 810 (e.g., any of microprocessors, controllers, and the like), which process various computer-executable instructions to control the operation of computing system 800 and to enable techniques for, or in which can be embodied, determining health state trends for a consistent patient situation. Alternatively or in addition, computing system 800 can be implemented with any one or combination of hardware, firmware, or fixed logic circuitry that is implemented in connection with processing and control circuits which are generally identified at 812. Although not shown, computing system 800 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 800 also includes computer-readable media 814, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 800 can also include a mass storage media device 816.

Computer-readable media 814 provides data storage mechanisms to store device data 804, as well as various device applications 818 and any other types of information and/or data related to operational aspects of computing system 800. For example, an operating system 820 can be maintained as a computer application with computer-readable media 814 and executed on processors 810. Device applications 818 may include a device manager, such as any form of a control application, software application, signal-processing and control module, code that is native to a particular device, a hardware abstraction layer for a particular device, and so on.

Device applications 818 also include any system components, engines, or managers to implement the techniques. In this example, device applications 818 include health manager 210 or sensor manager 310.

CONCLUSION

Although embodiments of techniques for, and apparatuses enabling, determination of health state trends or disease progression for a consistent patient situation have been described in language specific to features and/or methods, it is to be understood that the subject of the appended claims is not necessarily limited to the specific features or methods described. Rather, the specific features and methods are disclosed as example implementations of these techniques.

What is claimed is:

1. A computer-implemented method comprising:
    detecting, using one or more sensing devices of a sensing milieu contained in a bedroom, an automobile, a bathroom, an office, or a workplace, a first instance of an activity of a patient that is within a normal course of life of the patient, wherein said detecting is passive in that no explicit patient interaction with any of said one or more sensing devices is required, wherein said sensing devices are part of a color-sensing mirror, a pressure and electrical sensing mat, an ultrasonic bathtub, or an automobile rear-view minor and sense in a first modality, wherein said detecting is non-invasive, and wherein said activity that is within the normal course of life of the patient is walking, eating, working, exercising, driving, or talking;
    responsive to said detecting said first instance of the activity, monitoring, using a radar-based monitoring device that senses in a second modality that is other than the first modality, said patient to detect a first health state of the patient associated with said activity, wherein said monitoring is carried out in temporal proximity to said first instance of the activity, wherein said monitoring is non-invasive, and wherein said monitoring is passive in that no explicit patient interaction with said radar-based monitoring device is required;
    subsequently detecting, using said one or more sensing devices, multiple subsequent instances of said activity of the patient that is within said normal course of life of the patient, said subsequently detecting being passive and non-invasive;
    subsequently monitoring, for each of said detected subsequent instances of said activity, said patient using said radar-based monitoring device to detect subsequent respective health states of the patient associated with said activity, wherein said subsequent monitoring is carried out in temporal proximity to said subsequent instances of the activity, respectively, and wherein said subsequent monitoring is non-invasive and passive;
    processing said first and subsequent health states of the patient to determine a health state trend of the patient for said activity; and
    providing the health state trend for said activity.

2. The computer-implemented method as recited in claim 1, wherein the first and subsequent health states are measures of an oxygen content of the patient's blood or cardiac rhythm of the patient's heart.

3. The computer-implemented method as recited in claim 1, wherein the first and subsequent health states are measures of a health of a physiological system of the patient, the physiological system being a cardiovascular, nervous, endocrine, muscular, skeletal, or integumentary system.

4. The computer-implemented method as recited in claim 1, wherein the first and second passively and noninvasively sensed senor data are sensed without piercing the patient's skin or orifice.

5. The computer-implemented method as recited in claim 1, wherein determining the health state trend includes determining a health state trend for a disease.

6. The computer implemented method as recited in claim 5, wherein determining the health state trend includes calculating an outcome of the disease based on actions performed by the patient.

7. A computing device comprising:
one or more computer processors; and
one or more computer-readable media having instructions stored thereon that, responsive to execution by the one or more computer processors, implements a health manager configured to:
detect, using one or more sensing devices of a sensing milieu contained in a bedroom, an automobile, a bathroom, an office, or a workplace, a first instance of an activity of a patient that is within a normal course of life of the patient, wherein said detecting is passive in that no explicit patient interaction with any of said one or more sensing devices is required, wherein said sensing devices are part of a color-sensing mirror, a pressure and electrical sensing mat, an ultrasonic bathtub, or an automobile rear-view mirror and sense in a first modality, wherein said detecting is non-invasive, and wherein said activity that is within the normal course of life of the patient is walking, eating, working, exercising, driving, or talking;
responsive to said detecting of said first instance of the activity, monitor, using a radar-based monitoring device that senses in a second modality that is other than the first modality, said patient to detect a first health state of the patient associated with said activity, wherein said monitoring is carried out in temporal proximity to said first instance of the activity, wherein said monitoring is non-invasive, and wherein said monitoring is passive in that no explicit patient interaction with said radar-based monitoring device is required;
subsequently detect, using said one or more sensing devices, multiple subsequent instances of said activity of the patient that is within said normal course of life of the patient, said subsequent detection being passive and non-invasive;
subsequently monitor, for each of said detected subsequent instances of said activity, said patient using said radar-based monitoring device to detect subsequent respective health states of the patient associated with said activity, wherein said subsequent monitoring is carried out in temporal proximity to said subsequent instances of the activity, respectively, and wherein said subsequent monitoring is non-invasive and passive;
process said first and subsequent health states of the patient to determine a health state trend of the patient for said activity; and
provide the health state trend for said activity.

8. The computing device as recited in claim 7, wherein the radar-based monitoring device provides a radar field configured to reflect from human tissue and penetrate non-human material via continuously modulated radiation, ultra-wide band radiation, or sub-millimeter-frequency radiation.

9. The computing device as recited in claim 8, wherein the health state trend is a skeletal-system health state trend of said patient.

10. The computing device as recited in claim 8, wherein the health state trend is a cardiovascular-system health state trend of said patient.

11. A noninvasive health-monitoring system comprising:
a milieu of radar-based health monitoring sensors, the milieu of radar-based health monitoring sensors part of a radar lamp or a color-sensing mirror;
one or more computer processors; and
one or more computer-readable media having instructions stored thereon that, responsive to execution by the one or more computer processors, implements a sensor manager configured to:
cause each of the milieu of radar-based health-monitoring sensors to repeatedly provide, through the radar-emitting element, radar fields;
repeatedly determine activities of a patient based on a patient's human-tissue reflection in the respective radar fields, the activities within the normal course of life and determined to be walking, eating, or talking;
repeatedly associate health states to the determined activities based on the patient's human-tissue reflection or another human-tissue reflection in the respective radar fields; and
provide the determined activities and the associated health states.

12. The noninvasive health-monitoring system as recited in claim 11, wherein the health states are skeletal system health states.

13. The noninvasive health-monitoring system as recited in claim 11, wherein the health states are cardiovascular system health states.

14. The noninvasive health-monitoring system as recited in claim 11 where the radar fields are provided as modulated radiation, ultra-wideband radiation, or sub-millimeter-frequency radiation.

15. The computer-implemented method as recited in claim 1, wherein the first modality includes reflected light, sound waves, electromagnetic sensing, or fluid mechanics.

16. The computer-implemented method as recited in claim 1, where the radar-based monitoring device that senses in the second modality senses using a radar field that includes modulated radiation.

17. The computer-implemented method as recited in claim 1, where the radar-based monitoring device that senses in the second modality senses using a radar field that includes ultra-wideband radiation.

18. The computer-implemented method as recited in claim 1, where the radar-based monitoring device that senses in the second modality senses using a radar field that includes sub-millimeter-frequency radiation.

19. The computing device as recited in claim 7, wherein the said sensing devices that are part of a color-sensing mirror, a pressure and electrical sensing mat, an ultrasonic bathtub, or an automobile rear-view mirror include fiber optics, piezoelectric materials, or a camera.

20. The computing device as recited in claim 19, wherein the camera is a color-sensing camera.

\* \* \* \* \*

UNITED STATES PATENT AND TRADEMARK OFFICE
CERTIFICATE OF CORRECTION

| | |
|---|---|
| PATENT NO. | : 10,216,905 B2 |
| APPLICATION NO. | : 15/008295 |
| DATED | : February 26, 2019 |
| INVENTOR(S) | : Jeffrey L. Rogers |

Page 1 of 1

It is certified that error appears in the above-identified patent and that said Letters Patent is hereby corrected as shown below:

Column 14, Line 35, Claim 1 after "rear-view" before "and" delete "minor" insert --mirror--

Signed and Sealed this
Twenty-sixth Day of March, 2019

Andrei Iancu
*Director of the United States Patent and Trademark Office*